United States Patent [19]

Franzen et al.

[11] Patent Number: 4,727,202
[45] Date of Patent: Feb. 23, 1988

[54] PROCESS FOR THE PRODUCTION OF CATALYTICALLY-ACTIVE METALLIC GLASSES

[75] Inventors: Volker Franzen, Basel; Hans-Joachim Güntherodt, Witterswil; Alfons Baiker, Glattbrugg; Erich Armbruster, Allschwil; Halim Baris, Dübendorf, all of Switzerland

[73] Assignee: Lonza Ltd., Gampel, Switzerland

[21] Appl. No.: 51,183

[22] Filed: May 18, 1987

Related U.S. Application Data

[60] Continuation of Ser. No. 833,239, Feb. 27, 1986, abandoned, Division of Ser. No. 758,829, Jul. 25, 1985, abandoned.

[30] Foreign Application Priority Data

Jul. 27, 1984 [CH] Switzerland ............... 3679/84

[51] Int. Cl.$^4$ .................................. C07C 5/03
[52] U.S. Cl. ............................ 585/259; 585/271; 585/273; 585/275; 585/262
[58] Field of Search ............... 585/259, 271, 273, 275, 585/262

[56] References Cited

U.S. PATENT DOCUMENTS

| | | |
|---|---|---|
| 670,775 | 3/1901 | Gesner . |
| 1,735,763 | 11/1929 | Jaeger . |
| 2,744,062 | 5/1956 | Marshall ........................ 204/10 |
| 3,259,324 | 7/1966 | Ball et al. ...................... 241/17 |
| 3,363,846 | 12/1965 | Eck ................................ 241/15 |
| 3,376,107 | 4/1968 | Oka ............................... 23/204 |
| 3,856,513 | 12/1974 | Chen et al. ..................... 75/122 |
| 3,872,836 | 3/1975 | Polk et al. ...................... 29/194 |
| 3,981,722 | 9/1976 | Ray et al. ....................... 75/122 |
| 3,986,867 | 10/1976 | Masumoto et al. . |
| 3,989,517 | 11/1976 | Tanner et al. ................. 75/175.5 |
| 3,992,476 | 11/1976 | Rausch ........................... 260/683 |
| 4,018,839 | 4/1977 | Rausch ........................... 260/666 |
| 4,179,581 | 12/1979 | Mitsche ......................... 585/744 |
| 4,197,146 | 4/1980 | Frischmann ................... 148/31.55 |
| 4,201,837 | 5/1980 | Lupinski ........................ 428/457 |
| 4,304,593 | 12/1981 | Maeland ........................ 75/0.5 |
| 4,409,410 | 10/1983 | Cosyns et al. ................. 585/259 |

FOREIGN PATENT DOCUMENTS

0034403 8/1981 European Pat. Off. .

OTHER PUBLICATIONS

Erich Armbruster, et al., "Ammonia Synthesis Over a Novel Catalyst Prepared from an amorphous $Fe_{91}Zr_9$ Precursor", J. Chem. Soc. Chem., Commun., No. 4, pp. 299-301.

Alfon Baiker et al., "Novel Hydrogenation Catalyst Prepared from an Amorphous ... Precursor", J. Chem. Soc. Chem. Commun., No. 12, (1986) p J. L. Reilly et al., "Formation and Properties of Iron Titanium Hydride, Inorganic Chem., vol. 13, No. 1, (1974) pp. 218-222.

Polesya et al., Izv, Akad, Navk. SSR, Metal, No. 6, (1973), pp. 173-178.

Ray et al., Metallurgical Transactions, vol. 3, (Mar. 1972) pp. 627-629.

Cocke, D. L., et al., "Catalysis by Amorphous Materials", Rapidly Quenched Metals, Elsevier Science Publishers D. V., vol. II (proceeding of Sep. 3 to 7, 1984) pp. 1497 to 1503.

Duwez, Pol. et al., J. of Applied Physics 31, (1960), pp. 1136 and 1137.

Ruhl, R. C., Mat. Sci. & Eng. 1 (1967), pp. 313 to 320.

Schloegl, Robert, "Application of Amorphous Metals in Heterogenous Catalysis", Rapidly Quenched Metals, Elsevier Science Publishers D. V., vol. II (Proceeding of Sep. 3 to 7, 1984), pp. 1497-1503.

G. V. Smith et al., Journal of Catalysis, 83, 1983, pp. 238-241.

A. Yokoyama et al., Chemistry Letters, 1983, pp. 195-198.

B. Giessen et al., Materials Research Society Symposia Proceedings, (1982), vol. 18, pp. 255-258.

Gubanov A. I., Soviet Physics-Solid State, vol. 2, (1960), pp. 468-471.

Duwez, Pol. Fizika Z. Suppl. 2 (1970), pp. 1.1 to 1.15, 47.1 and 48.1.

*Primary Examiner*—Curtis R. Davis
*Attorney, Agent, or Firm*—Fisher, Christen & Sabol

[57] ABSTRACT

Catalytically-active metallic glasses containing at least one element from a subgroup of the periodic system and at least one element from a main group of the periodic system. Process for the production of catalytically-active metallic glasses where the metallic glass is produced from at least one element from a subgroup of the periodic system and at least from one element from a main group of the periodic system. The metallic glasses are activated by self-activation or by an oxidative and-/or reductive treatment. The catalytically-active metallic glasses can be used as hydrogenation, oxidation or isomerization catalysts.

13 Claims, No Drawings

PROCESS FOR THE PRODUCTION OF CATALYTICALLY-ACTIVE METALLIC GLASSES

This is a continuation of application ser. No. 833,239, filed on Feb. 27, 1986, now abandoned which is a division of application ser. No. 758,829, filed on July 25, 1985 pending.

BACKGROUND OF THE INVENTION

1. Field of the Invention

The invention relates to catalytically-active metallic glasses, process of producing such metallic glasses and process of using such metallic glasses.

2. Prior Art

Certain amorphous metal alloys catalyze hydrogenation reactions, for example, those of cyclohexene derivatives [G. V. Smith et al., J. of Catalysis 83 (1983) 238] or of carbon monoxide (i.e., Fisher-Tropsch Reaction) [A. Yokoyama et al., Chemistry Letters (1983), 195]. The catalytic action is based on the amorphous state of the metals. However, it has also been described that in the case of the system $Pd_{80}Si_{20}$, no significant differences exist concerning the selectivity in the case of hydrogenation reactions between the amorphous state and the crystalline state [B. Giessen et al., Mater. Res. Soc. Symp. Proc., (1982), Vol. 18, 255].

In the case of most examinations, the surfaces and the state of order of the catalysts consisting of amorphous metals have not been investigated sufficiently, so that the comparison between amorphous and crystalline systems is not of any significant meaning. It turned out, for example, that the catalytical effectiveness could not be deduced because of a lack of knowledge of the connections between amorphous and crystalline systems.

BROAD DESCRIPTION OF THE INVENTION

An object of the invention is to provide processes for the production of catalytically-active metallic glasses. Another object of the invention is to provide such catalytically-active metallic glasses. A further object of the invention is to provide processes for the use of such catalytically-active metallic glasses. Other objects and advantages of the invention are set out herein or obvious herefrom to one skilled in the art.

The objects and advantages of the invention are achieved by the processes and metals of the invention.

It is to be noted that in the present terminology, metallic glasses are to have the same meaning as amorphous metals.

The invention involves a process for the production of catalytically-active metallic glasses from at least one element from one of the subgroups of the periodic system and at least from one element from one of the main groups of the periodic system. The metallic glasses are activated by self-activation or by an oxidative and/or reductive treatment.

According to the process of the invention, the metallic glasses change in such a way that the transformation products, the nature of which has not yet been described exactly, show unexpected catalytical effectiveness. Possibly, amorphous and crystalline regions lie side by side in highly dispersed forms. It is further noteworthy that the composition of the surface in many cases is not the same as that of the (mass) mass.

Starting out from amorphous alloys, catalysts according to the process of the invention can be produced which are not obtainable according to the hitherto known methods and processes for the production of catalysts or from the corresponding crystalline alloys.

The advantage of using amorphous metals as a starting material for the production of catalysts according to the process of the invention rests, among other things, on the fact that the metals in their amorphous state are distributed in an extraordinarily highly-dispersed manner; they may be aggregations of only a few atoms. In the case of the processes for the production of catalysts used hitherto, it is true that with regard to the degree of dispersions, great advances have been achieved, however, none of the industrially used processes leads to a similarly high degree of dispersion as obtained by the process of the invention.

According to the invention, the catalytically-active metallic glasses contain at least one element from at least one of the subgroups of the periodic system and at least one element from at least one of the main groups of the periodic system. In the invention, the elements of Group VA are also counted as being in the main groups.

The metallic glasses according to the invention can contain an element from Group IVA of the periodic system and at least one element of Group IB, Group VA or Group VIII of the periodic system. From Group IV, the elements Ti and especially Zr, from Group IB the element Cu, from Group VA, the element V (vanadium), and from Group VIII, the elements Co, Ni, Pd and especially Fe, are preferred.

The designation of the groups of the periodic system herein, and the accompanying claims, is based on the Table "The Periodic System Of the Elements" from "Roempps Chemical Dictionary," Vol. 4, 7th Ed., (1974), page 2557.

Suitable metallic glasses contain Zr and Fe, Ti and Fe, Zr and Cu, Ti and Cu, Zr and V, Ti and V, Zr and Ni, or Ti and Ni, and preferably they consist of metals with the formula $Fe_{91}Zr_9$, with the formula $Fe_{91}Ti_9$, with the formula $Fe_{24}Zr_{76}$, with the formula $Fe_{24}Ti_{76}$, with the formula $Ni_{24}Zr_{76}$ or $Ni_{24}Ti_{76}$, with the formula $Cu_{70}Zr_{30}$ or $Cu_{70}Ti_{30}$, with the formula $V_{36}Zr_{64}$ or $V_{36}Ti_{64}$, or with the formula $Ni_{64}Zr_{36}$ or $Ni_{64}Ti_{36}$.

The so-called metallic glasses, amorphous metals, glassy metals or vitreously-rigidified metals according to the invention are amorphous metal alloys with a disarranged structure which are not located in the thermodynamic equilibrium. Metallic glasses are inclined to recrystallization whenever the reaction temperature of the catalytic conversion lies above the vitreous conversion temperature. As a result of component of the alloy, with up to 5 atom percent, for example, of molybdenum or tungsten, the glass conversion temperature can be raised so far that a stabilization of the actual catalyst is achieved without significantly influencing its activity. Stabilized, metallic glasses consist, for example, of Zr or Ti, Fe and Mo, preferably with the formula $(Fe_{91}Ti_9)_{95}—Mo_5$ or $(Fe_{91}ZR_9)_{95}—Mo_5$.

The catalytically-active, metallic glasses can be used as such as catalysts since they often activate themselves, partly with an enlargement of the surface; an example of such a metal has the formula $Fe_{91}Zr_9$ or $Fe_{91}Ti_9$.

It can, however, also be effective for various metallic glasses, for example, $Ni_{64}Zr_{36}$ or $Ni_{64}Ti_{36}$, to conduct catalyst activation—such is within the scope of the invention. Such catalyst activations comprise processes such as treating with acids, effectively diluted acids, preferably aqueous $HNO_3$, in order to remove layers of oxide, then subsequently treating with oxygen and after that treating with hydrogen. Consequently, the activation consists of treatment in an oxidizing atmosphere and subsequently treatment in a reducing atmosphere. Corresponding to the intended purpose of use, the treatment can also be reversed.

The metallic glasses, therefore, amorphous metals of the invention are also suitable as starting products for catalysts without carriers. For example, one of the phases can be convert by chemical conversion in such a way that it acts like a carrier in the conventional sense. As a possible disadvantage, there is a smaller specific surface which results from the various production processes.

The metallic glasses can be produced in known manners, for example, by the melt spinning process, as flat or separated lamellae, and by the splat-cooling process.

It turned out, however, that the ribbons obtained according to the melt-spinning process are also easily reduced to powder at low temperature and so can also be used in powdery form. Metallic glasses or amorphous metals, however, can also be produced directly as a powder. From ribbons or foils of metallic glass or amorphous metal, molded bodies, for example, filles of columns, can also be produced and then activated to a catalyst state, being used as such.

In a series of cases, for example, with $Cu_{70}Zr_{30}$ or $Cu_{70}Ti_{30}$, the catalysts from metallic glasses show activity already at temperatures lower than the corresponding catalysts based on crystalline starting material. It is important that the reaction temperature be sufficiently lower than the glass conversion temperature of the metallic glass.

The metallic glasses of the formula $Cu_{70}Zr_{30}$ can be activated in a hydrogen stream and then are suitable as hydrogenation catalysts, for example, for the hydrogenation of 1,3-butadiene. For this reaction, it is advantageous to reduce the metallic glasses with the formula $Cu_{70}Zr_{30}$ for about 2 to 8 hours in a hydrogen stream at 160° to 240° C. During the hydrogenation a ratio of butadiene to hydrogen of 2:1 to 1:1 and a temperature of 90° to 200° C., preferably 95° to 130° C., is maintained.

The catalysts produced according to the invention from the metallic glasses are suitable for hydrogenation reactions, for example, the synthesis of ammonium from hydrogen and nitrogen, of hydrocarbons from olefins or hydrogenation from nitroaromatics, for example, of cyclic hydrocarbon, such as toluene, and for isomerizations, for example, methylcyclopentane.

By way of summary, the invention involves catalytically-active metallic glasses composed of at least one element from Group IVA of the periodic system, for example, Zr or Ti, and at least one element from Group IB, for example, Cu, or Group VA, for example, V, or Group VIII, for example, Co, Ni, Pd or Fe. The metallic glasses have been self-activated or activated by an oxidative and/or reductive treatment. The metallic glasses can be used as catalysts, for example, for hydrogenation, oxidation or isomerization.

DETAILED DESCRIPTION OF THE INVENTION

As used herein, all ratios, proportions, parts and percentages are on a weight basis unless otherwise stated herein or otherwise obvious herefrom to one skilled in the art.

EXAMPLE 1

Synthesis of ammonium from nitrogen and hydrogen

For the conversion, a gas of 75 percent of hydrogen and 25 percent of nitrogen was used. The gas mixture was free of carbon monoxide. The pressure was 9 bar. In a microcontinuous reactor, 2 g of catalyst was inserted. The length of the catalyst bed was 20 mm, and the through-flow quantity was between 20 and 200 micromole $sec^{-1}$.

TABLE I

| Starting material | Steady-State turnover nanomole $sec^{-1}$ | | | Remarks |
| --- | --- | --- | --- | --- |
| | 380° C. | 400° C. | 420° C. | |
| Conventional Halder-Topsoe catalyst | 250 | 450 | 700 | after 2000 hrs. not stable |
| $Fe_{91}Zr_9$-crystalline | 800 | 1400 | 2000 | stable after 2000 hrs. |
| $Fe_{91}Zr_9$-crystalline | 140 | 260 | 400 | stable after 2000 hrs. |
| $(Fe_{91}Zr_9)_{95}$-$Mo_5$ glass | 180 | 330 | 500 | stable |
| $Ni_{64}Zr_{36}$ glass | 190 | 340 | 600 | |

A nickel-zircon catalyst produced in the conventional manner showed no effectiveness under these conditions. Under steady-state turnover, the turnover is given per contact time standardized on the surface of the starting materials (equals average duration of stay of a gas molecule in the contact volume). The Halder-Topsoe catalyst is more sensitive vis-a-vis oxygen than the $Fe_{91}Zr_9$ glass.

EXAMPLE 2

Synthesis of ammonium

The conversion was carried out in an integral reactor made of stainless steel (40 cm long, 1.5 cm diameter) with purified gases. Analysis of the reaction products was done by means of an IR-gas analyzer. The pressure was 4 bar. The total through-flow of gas was 30 to 40 $ml_N.min^{-1}$ with a catalyst quantity of 8 to 10 g. The ribbons of metallic glass or amorphous metal were degreased and cut into pieces of a length of 1 to 2 cm.

TABLE II

| Starting Material | Temp., °C. | Conversion grade $n = \frac{[NH_3]}{[NH_3] \ (eq)}$ |
| --- | --- | --- |
| $Fe_{91}Zr_9$, amorphous | 350° | 0.001704 |
| $Fe_{91}Zr_9$, crystalline | 350° | 0.001309 |
| Fe, pure crystalline | 380° | 0.000144 |
| $Fe_{91}Zr_9$, amorphous | 380° | 0.005089 |
| $Fe_{91}Zr_9$, crystalline | 380° | 0.004801 |
| Fe, pure crystalline | 450° | 0.00835 |
| $Fe_{91}Zr_9$, crystalline | 450° | 0.03268 |
| $Fe_{24}Zr_{76}$, amorphous | 450° | 0.08170 |
| $Fe_{24}Zr_{76}$, amorphous | 380° | 0.002880 |

Note:
Ratio $N_2:H_2 = 1:2$

That alternating effects exist between the metals in the actual effective catalyst is shown in the comparison of the conversion figures for the ammonium synthesis in the case of the system iron-zirconium. Whereas pure iron does not result in an active catalyst at 350° C., $Fe_9Zr_{91}$ and $Fe_{24}Zr_{76}$ glasses form active catalysts. Whereas $Fe_{91}Zr_9$ is more active at 400° C. than $Fe_{24}Zr_{76}$, $Fe_{24}Zr_{76}$ surpasses the activity of $Fe_{91}Zr_9$ at higher temperatures. Many highly active catalytic systems can be obtained by way of amorphous metals.

EXAMPLE 3

Hydrogenation of ethylene

The investigation was carried out in a circulation reactor, and the products were analyzed by means of gas chromatography. The metallic glasses or amorphous metals were used as strips of about 1 cm length after they had been degreased. The reaction mixture consisted of ethylene and hydrogen. Amorphous $Ni_{64}Zr_{36}$ was first treated with diluted nitric acid, then treated with oxygen and subsequently treated with hydrogen. After this pretreatment, the material showed catalytic activity. $Fe_{91}Zr_9$ glass showed no activity even after the pretreatment. $Cu_{70}Zr_{30}$ glass showed a clear enlargement of its surface and extraordinary catalytic activity by means of treatment with hydrogen.

TABLE III

| Catalyst | Reduction | Activity |
| --- | --- | --- |
| $Cu_{70}Zr_{30}$ amorphous | 200° C. $H_2$, 4 hrs. | very active even at 80° C. |
| $Cu_{70}Zr_{30}$ crystalline | 200° C. $H_2$, 4 hrs. $H_2$, 8 hrs. | — — |
| Cu | 200° C. $H_2$, 4 hrs. | — |

With amorphous $Cu_{70}Zr_{30}$, after activation at 200° C., a parallel quantitative conversion was measured in 24 minutes. In the same period of time, the conversion already was 40 percent at 80° C. The difference between amorphous and crystalline starting material showed itself very clearly in the case of hydrogenation of ethylene by means of $Cu_{70}Zr_{30}$. Only the amorphous starting material resulted in an active catalyst.

EXAMPLE 4

Oxidation of toluene

The conversion was carried out with a micropulse reactor at 300° C. The reactor was coated with 2 g of amorphous $V_{36}Zr_{64}$, which previously had been treated with diluted $HNO_3$. A stream of air was saturated with toluene and was passed through the micropulse reactor. After 2 hours, the catalyst had activated itself; per passage, 12.5 percent of the toluene quantity used was oxidized into benzoic acid.

Under identical conditions, a $V_2O_5$ catalyst on $SiO_2$ resulted in a conversion of 8.9 percent.

EXAMPLE 5

Hydrogenation of 1,3-butadiene

The reactions were carried out in a batch-circulation reactor and the products consisting of 1-butene, cis-2-butene, trans-2-butene and butane were analyzed by means of gas chromatography. Amorphous and crystalline samples of the composition $Cu_{70}Zr_{30}$ were reduced at 200° C. for 4 hours in a stream of hydrogen. This pretreatment caused an enlargement of the surface of 0.015 m²/g on 0.56 m²/g with the amorphous sample, while the surface of the crystalline sample remained unchanged at 0.008 m²/g.

In order to be able to compare the activity of these samples, catalyst quantities were selected such that equally large surfaces were present in the reactor. Under identical conditions (T=130° C., p=0.8 bar, butadiene:$H_2$=1:1), these experiments clearly showed that amorphous $Cu_{70}Zr_{30}$ was much more active than the corresponding crystalline sample.

TABLE IV

| t (min). | 0.12 g of amorphous, conversion, percent | 8.0 g of crystalline conversion, percent |
| --- | --- | --- |
| 25 | 4.59 | 0.0 |
| 70 | 13.04 | 0.0 |
| 90 | 16.76 | 0.0 |
| 130 | 23.00 | 0.9 |
| 130 | 26.00 | 1.1 |

The selectivity as to butene was more closely investigated with the amorphous sample. In the case of 90 percent conversion, the selectivity was 75 percent at 130° C. and 96 percent at 95° C.

EXAMPLE 6

Selective hydrogenation of butadiene

Dienes, especially 1,3-butadiene, cause deactivation of the catalyst in the case of hydroformylation and form polymers in cracking operations. Therefore, they should be removed from olefins.

According to Example 5, 4 g of amorphous $Cu_{70}Zr_{30}$ was used as catalyst. The hydrogenation of the mixture with the composition: 73 percent of 1-butene, 24 percent of cis-2-butene and 3 percent of 1,3-butadiene, was examined at various temperatures. At temperatures higher than 90° C., olefins were hydrogenated and large quantities of butane developed. At 75° C., butadiene was hydrogenated selectively and the product distribution consisted of: 1.63 percent of butane, 1.35 percent of trans-2-butene, 22.6 percent of cis-2-butene, 74.41 percent of 1-butene and 0.0 percent of butadiene, after a reaction time of 80 minutes. The hydrogen concentration at the same time was 2 to 4 times greater than the butadiene concentration. In this area, the hydrogen concentration had no greater influence on the selectivity. The selective hydrogenation of butadiene in the mixture of ethylene and butadiene also took place at lower temperatures. The reaction temperature of 75° C. made possible the hydrogenation of butadiene with 93 percent selectivity on butene; ethylene was not hydrogenated at all. Higher temperatures however also cause the hydrogenation of ethylene.

What is claimed is:

1. Process for the hydrogenation of olefins comprising catalytically hydrogenating at least one olefin by contacting said at least one olefin in the presence of hydrogen with an activated, vitreously-rigidified, metallic glass at a temperature and pressure which are effective to achieve said hydrogenation, said metallic glass being present in an amount effective to catalytically effect said hydrogenation, said metallic glass consisting of at least one element from Group IV A of the periodic system and at least one element from Group I B, Group V A and/or Group VIII of the periodic system, said catalyst being activated before said hydrogenation step by subjecting said catalyst to an oxidative and/or reductive treatment or said catalyst being activated in situ during said hydrogenation step by said at least one olefin and/or said hydrogen.

2. Process as claimed in claim 1 wherein the olefin is 1,3-butadiene and the metallic glass consists of $Cu_{70}Zr_{30}$.

3. Process as claimed in claim 2 wherein the hydrogenation is conducted at a temperature of 90° C. to 200° C. and the ratio of 1,3-butadiene to hydrogen is 2:1 to 1:1.

4. Process as claimed in claim 2 wherein the $Cu_{70}Zr_{30}$ has been activated in situ.

5. Process as claimed in claim 1 wherein the metallic glass consists of Zr and at least one element from Group I B, Group V A and/or Group VIII of the periodic system.

6. Process as claimed in claim 1 wherein the metallic glass consists of $Cu_{70}Zr_{30}$.

7. Process as claimed in claim 1 wherein the hydrogenation is conducted at a temperature of 90° to 200° C.

8. Process as claimed in claim 1 wherein the ratio of olefin to hydrogen is 2:1 to 1:1.

9. Process as claimed in claim 1 wherein the metallic glass consists of $Cu_{70}Zr_{30}$ has been activated with hydrogen.

10. Process as claimed in claim 1 wherein the metallic glass consists of $Cu_{70}Zr_{30}$ or $Cu_{70}Ti_{30}$ has been activated by treatment with an acid, then with oxygen and followed with hydrogen.

11. Process as claimed in claim 10 wherein the acid is $HNO_3$.

12. Process as claimed in claim 1 wherein the olefin is 1,3-butadiene.

13. Process as claimed in claim 1 wherein said at least one olefin is a mixture of at least one mono-olefin and at least one diolefin and wherein said at least one diolefin is selectively hydrogenated as opposed to said at least one mono-olefin.

* * * * *

UNITED STATES PATENT AND TRADEMARK OFFICE
CERTIFICATE OF CORRECTION

PATENT NO. : 4,727,202

DATED : February 23, 1988

INVENTOR(S) : Volker Franzen et al.

It is certified that error appears in the above-identified patent and that said Letters Patent is hereby corrected as shown below:

On the title page

[60] Continuation of Ser. No. 833,239, Feb. 27, 1986, abandoned, Division of Ser. No. 758,829, Jul. 25, 1985.

Signed and Sealed this

Twenty-seventh Day of December, 1988

Attest:

DONALD J. QUIGG

*Attesting Officer*    *Commissioner of Patents and Trademarks*